(12) United States Patent
Fitzgerald

(10) Patent No.: US 7,206,376 B2
(45) Date of Patent: Apr. 17, 2007

(54) FLUID DENSITY MEASUREMENT

(75) Inventor: John Barry Fitzgerald, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 93 days.

(21) Appl. No.: 10/493,592

(22) PCT Filed: Oct. 31, 2002

(86) PCT No.: PCT/GB02/04924

§ 371 (c)(1), (2), (4) Date: Sep. 16, 2004

(87) PCT Pub. No.: WO03/042666

PCT Pub. Date: May 22, 2003

(65) Prior Publication Data

US 2005/0031074 A1 Feb. 10, 2005

(30) Foreign Application Priority Data

Nov. 10, 2001 (GB) .................. 0127071.9

(51) Int. Cl.
*G01N 23/083* (2006.01)
*G01V 5/12* (2006.01)

(52) U.S. Cl. .................. 378/54; 250/266; 250/269.3; 250/364; 73/152.14

(58) Field of Classification Search ............ 378/51–56; 250/266, 269.3, 364; 73/152.14
See application file for complete search history.

(56) References Cited

U.S. PATENT DOCUMENTS 3,780,575 A   12/1973   Urbanosky
(Continued)

FOREIGN PATENT DOCUMENTS

FR   2 605 738 A1   4/1988
(Continued)

*Primary Examiner*—Allen C. Ho
(74) *Attorney, Agent, or Firm*—Edward M. Bushard; Steven Gahlings; Tim W. Curington

(57) ABSTRACT

A wellbore tool for measuring the density of a fluid flowing in a wellbore by a photon attenuation technique includes a tube defining a flow path for the fluid, a photon source at one end of the tube, and a photon detector arranged to receive photons which have passed along the tube. In a preffered implementation, a source which emits coincident photon pairs, preferably $^{22}$Na, is used. In this embodiment, the tube defining the fluid flow path has first and second relatively straight and aligned measurement portions disposed on opposite sides of the photon source, so that each measurement portion receives a respective photon of some of the coincident pairs for transmission longitudinally along it. Respective detectors at the other ends of the measurement portions receive respective ones of the photon pairs. The detected coincident photons are counted, and the density of the fluid is derived from the count rate.

12 Claims, 4 Drawing Sheets

U.S. PATENT DOCUMENTS

| | | | |
|---|---|---|---|
| 3,787,683 A * | 1/1974 | Kishel | 250/308 |
| 3,859,851 A | 1/1975 | Urbanosky | |
| 3,898,463 A * | 8/1975 | Noakes | 250/367 |
| 3,924,125 A * | 12/1975 | Murray | 250/303 |
| 4,016,418 A * | 4/1977 | Horrocks et al. | 250/252.1 |
| 4,492,865 A | 1/1985 | Murphy et al. | |
| 4,860,581 A | 8/1989 | Zimmerman et al. | |
| 4,936,139 A | 6/1990 | Zimmerman et al. | |
| 5,008,906 A | 4/1991 | Reichwein | |
| 5,065,417 A | 11/1991 | Behringer et al. | |
| 5,083,026 A * | 1/1992 | Elbaum | 250/369 |
| 5,120,955 A * | 6/1992 | Galford | 250/256 |
| 5,180,916 A * | 1/1993 | Lehtinen et al. | 250/367 |
| 5,361,632 A | 11/1994 | Magnani | |
| 5,408,097 A * | 4/1995 | Wraight et al. | 250/256 |
| 5,487,880 A * | 1/1996 | Taylor et al. | 423/2 |
| 5,866,907 A * | 2/1999 | Drukier et al. | 250/366 |
| 5,880,375 A * | 3/1999 | Bielski et al. | 73/861.05 |
| 6,011,263 A * | 1/2000 | Bielski et al. | 250/356.1 |

FOREIGN PATENT DOCUMENTS

| | | |
|---|---|---|
| GB | 2 351 810 A | 1/2001 |
| GB | 2 351 810 B | 8/2001 |
| WO | 97/29356 A1 | 8/1997 |
| WO | 03/042666 A2 | 5/2003 |
| WO | 2003/042666 A3 | 5/2003 |

* cited by examiner

FLUID DENSITY MEASUREMENT

This invention relates to methods and apparatus for fluid density measurement, and is more particularly but not exclusively concerned with the measurement of the density of fluids flowing in a wellbore.

In the evaluation of a hydrocarbon reservoir surrounding a wellbore, it is very useful to be able to measure the density of the fluid flowing from the reservoir and along the wellbore. One known technique for measuring fluid density is a transverse photon attenuation measurement, in which the attenuation of gamma ray photons passing transversely through a pipe containing the fluid is measured: such a technique is disclosed in our United Kingdom Patent Application No. 2,351,810. However, the technique disclosed in that patent application is primarily intended for use in locations where spatial constraints are not too severe. In deep wellbores of relatively small diameter, and in certain wellbore tools, the space available for the apparatus required for such a measurement can be extremely limited.

For example, Schlumberger has developed a commercially successful wellbore tool called a Modular Formation Dynamics Tester, usually abbreviated to MDT, which analyses formation fluids. The MDT withdraws and analyses a flow stream of formation fluids generally as described in U.S. Pat. Nos. 3,859,851, 3,780,575, 4,860,581 and 4,936,139. It would be desirable to provide the MDT with a module for measuring fluid density. However, the space available within an MDT is determined by its internal diameter, which is about 9 cm. Given the need for substantial wall thickness for the pipe in which the fluid flows and for the housing for the photon source and detector in view of the high fluid pressures typically encountered, the maximum internal diameter of the pipe containing the fluid in an MDT module, and therefore the maximum dimension of the fluid path over which such a transverse photon attenuation measurement could be made, would be extremely small, typically not more than about 5 to 10 mm. This would make the measurement relatively insensitive to the density of the fluid. Locally increasing the internal diameter of pipe, even if possible, is not likely to be helpful, since it may well lead to sudden local expansion of the fluid, which can change the properties of the fluid in a way which affects the validity of the density measurement.

The problems caused by the lack of space in certain wellbore applications for fluid density measuring apparatus based on photon attenuation are compounded by the fact that, in apparatus intended for use in a wellbore, it is extremely desirable for operational and safety reasons to use a low activity photon source of the kind exempt from licensing requirements. The use of such a low activity source substantially increases the time required to make a density measurement of the required statistical precision, during which time the density of the fluid may change significantly.

It is therefore an object of the present invention to provide methods and apparatus which are suitable for measuring the density of fluid flowing in a wellbore using a photon attenuation technique, and in which the abovementioned problems are alleviated.

According to a first aspect of the present invention, there is provided apparatus for measuring the density of a fluid, the apparatus comprising:

means defining a flow path for the fluid;

a photon source;

photon detector means positioned to receive photons from the photon source via the fluid in said flow path; and means for determining the density of the fluid from a count rate of the photons received by the detector means;

wherein said flow path includes a substantially straight measurement portion extending in the direction of flow of the fluid, the photon source is positioned at one end of said measurement portion, and the photon detector means is positioned at the other end of said measurement portion to receive photons which have passed along said measurement portion.

According to a second aspect of the invention, there is provided apparatus for measuring the density of a fluid, the apparatus comprising:

means defining a flow path for the fluid;

a photon source;

photon detector means positioned to receive photons from the photon source via the fluid in said flow path; and means for determining the density of the fluid from a count rate of the photons received by the detector means;

wherein the photon source comprises a source which emits coincident photon pairs, the flow path comprises two relatively straight measurement portions each disposed to receive a respective photon of each pair, the detector means comprises two detectors each arranged to receive photons which have passed along a respective measurement portion, and the density determining means determines the density of the fluid from the count rate of coincident photon pairs detected by the detectors.

Advantageously, the two measurement portions are substantially aligned with each other and spaced apart, and the source is disposed between their adjacent ends. Conveniently, the two measurement portions are substantially equal in length.

In a preferred implementation of the second aspect of the invention, the source comprises a positron emitter such as $^{22}$Na.

According to a third aspect of the invention, there is provided apparatus for measuring the density of a fluid, the apparatus comprising:

means defining a flow path for the fluid;

a photon source;

photon detector means positioned to receive photons from the photon source via the fluid in said flow path; and means for determining the density of the fluid from a count rate of the photons received by the detector means;

wherein the photon source is $^{22}$Na.

Advantageously, the apparatus further comprises means responsive to the photon detector means for counting the detected additional photons emitted on the de-excitation of the $^{22}$Ne daughter isotope resulting from the decay of the $^{22}$Na source, in which case the density determining means may be further arranged to determine the density of the fluid from the count rate of said detected additional photons.

The apparatus may further comprise means responsive to the photon detector means for measuring the count rate in the sum peak of the source, whereby to determine the activity of the source.

According to a fourth aspect of the invention, there is provided a method of measuring the density of a fluid, the method comprising the steps of:

defining a flow path for the fluid;

irradiating the fluid in the flow path with photons from a photon source;

detecting photons which have passed through the fluid in the flow path; and determining the density of the fluid from a count rate of the detected photons;

wherein said flow path includes a substantially straight measurement portion extending in the direction of flow of the fluid, the photon source is positioned at one end of said measurement portion, and the photon detector means is positioned at the other end of said measurement portion to receive photons which have passed along said measurement portion.

According to a fifth aspect of the invention, there is provided a method of measuring the density of a fluid, the method comprising the steps of:

defining a flow path for the fluid;

irradiating the fluid in the flow path with photons from a photon source;

detecting photons which have passed through the fluid in the flow path; and determining the density of the fluid from a count rate of the detected photons;

wherein the irradiating step comprises providing a photon source which emits coincident photon pairs, the flow path defining step comprises providing said flow path with first and second relatively straight measurement portions each disposed to receive a respective photon of each pair for transmission therealong, and the density determining step comprises determining the density of the fluid from the count rate of coincident photon pairs detected.

The density determining step may also comprise, for an upper part of the expected range of densities to be measured, determining the density of the fluid from the count rate of the photons passing along only one of said measurement portions.

The photon source used in the method is preferably $^{22}$Na, in which case the method preferably further comprises the step of counting the detected additional photons emitted on the de-excitation of the $^{22}$Ne daughter isotope resulting from the decay of the $^{22}$Na source, and may further include determining the density of the fluid from the count rate of the detected additional photons.

The method may additionally include measuring the count rate in the sum peak of the source, whereby to determine the activity of the source.

The invention will now be described, by way of example only, with reference to the accompanying drawings, of which:

Figure 1:
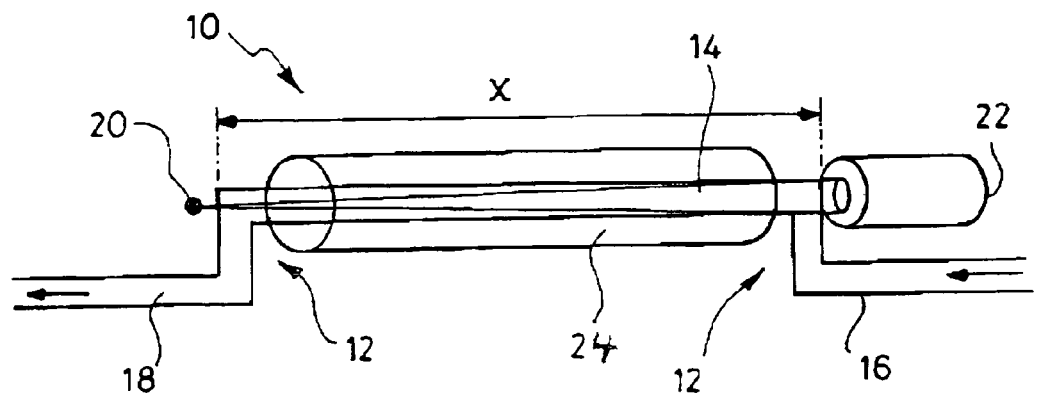
FIG. 1 is a simplified schematic representation of a wellbore tool for measuring the density of a fluid flowing in the wellbore by photon attenuation, in accordance with a first aspect of the present invention.

The wellbore tool illustrated in FIG. 1 is indicated generally at 10, and principally comprises a flow-line 12 shaped to define a substantially straight measurement portion 14 connected between laterally offset inlet and outlet portions 16, 18 which are substantially aligned and extend generally parallel to the measurement portion. As already mentioned, FIG. 1 is a simplified schematic representation of the tool 10, which in practice is mounted within a housing adapted to form a module for inclusion in an MDT. The MDT is in turn adapted to be lowered to a desired depth in the wellbore, e.g. on the end of a wireline or coiled tubing, and to extract formation fluids from the formations surrounding the borehole as described in the aforementioned United States patents.

Positioned at one end of the measurement portion 14 of the flow-line 12 is a low activity gamma ray photon source 20, for example a licence-exempt $^{133}$Ba source, while positioned at the other end of the measurement portion 14 is a photon detector 22, such as a combined NaI scintillator crystal and photomultiplier. The source 20 emits gamma ray photons, some of which pass longitudinally along the measurement portion 14 of the flow-line 12, through the fluid flowing in the measurement portion. A cylindrical collimator 24 made of a heavy metal such as lead or tungsten coaxially surrounds the measurement portion 14. The photons which have passed along the measurement portion 14 of the flow-line 12 are detected by the detector 22, and their count rate is measured as will become apparent hereinafter.

Since the attenuation of the photons passing along the measurement portion 14 of the flow-line 12 is dependent on the density of the fluid flowing along the measurement portion, the count rate of the photons detected by the detector 22 is also dependent on the density of the fluid. The relationship between the count rate, n, with fluid present, can be expressed as $$\frac{n}{n_0} = \exp(-\mu\rho x)$$

where $n_0$ is the count rate with no fluid present, $\mu$ is an attenuation coefficient which depends on the photon energy spectrum, $\rho$ is the fluid density and x is the attenuation path length, ie the length of the measurement portion 14.

Because the photons pass longitudinally along the flow-path 14, the attenuation path length can be made much greater than would be possible for the abovementioned prior art transverse photon attenuation measurement, typically up to about 30 cm. As a result, the density sensitivity of the tool 10 is considerably improved in relation to the density sensitivity which could be achieved with a transverse photon attenuation measurement effected under the same dimensional constraints.

Although the longitudinal photon attenuation measurement effected by the tool 10 is a substantial improvement over that obtainable if a transverse photon attenuation measurement were to be used in the tool, the longitudinal measurement nevertheless suffers from the disadvantage that the aperture of the measurement is very small. The preferred implementation of the invention illustrated in FIG. 2 is intended to alleviate this drawback.

Figure 2:
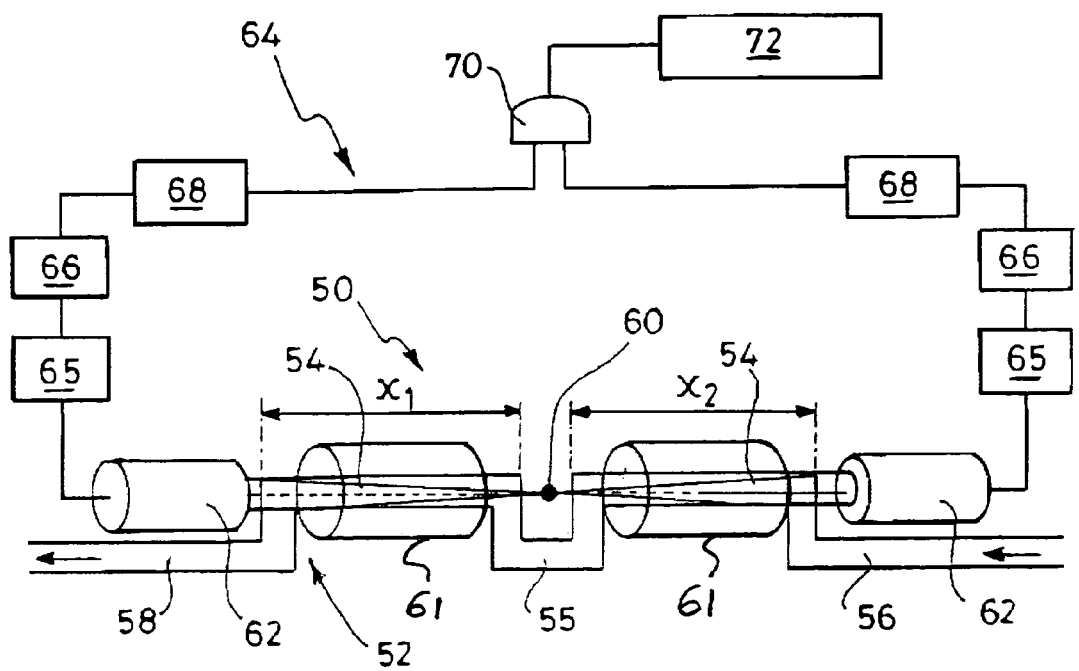
FIG. 2 is a simplified schematic representation of a wellbore tool for measuring the density of a fluid flowing in the wellbore by photon attenuation, using a photon source which emits coincident photon pairs, in accordance with a second and preferred aspect of the present invention.

Thus the wellbore tool of FIG. 2 is indicated generally at 50, and principally comprises a flow-line 52 shaped to define two substantially straight measurement portions 54, which are spaced apart, substantially axially aligned with each other, and connected in series with each other by a U-shaped connecting portion 55. The flow assembly comprising the measurement portions 54 and the connecting portion 55 is connected between laterally offset inlet and outlet portions 56, 58, which are substantially aligned and extend generally parallel to the measurement portions. As mentioned earlier, FIG. 2 is a simplified schematic representation of the tool 50, which, like the tool 10 of FIG. 1, is again in practice is mounted within a housing adapted to form a module for inclusion in an MDT. The MDT is in turn adapted to be lowered to a desired depth in the wellbore, eg on the end of a wireline or coiled tubing, and to extract formation fluids from the formations surrounding the borehole as described in the aforementioned United States patents.

Positioned between the adjacent ends of the measurement portions 54 of the flow-line 52, in the space defined by the limbs of the U-shaped connecting portion 55, is a low activity, licence-exempt, gamma ray photon source 60. But in the tool 50, the source 60 is a source which emits coincident photon pairs, preferably a positron emitter such as $^{22}$Na, although the use of other suitable multi-line gamma ray sources is also possible. Respective tubular collimators 61, each similar to the collimator 24 of FIG. 1, coaxially surround the measurement portions 54.

Figure 3:
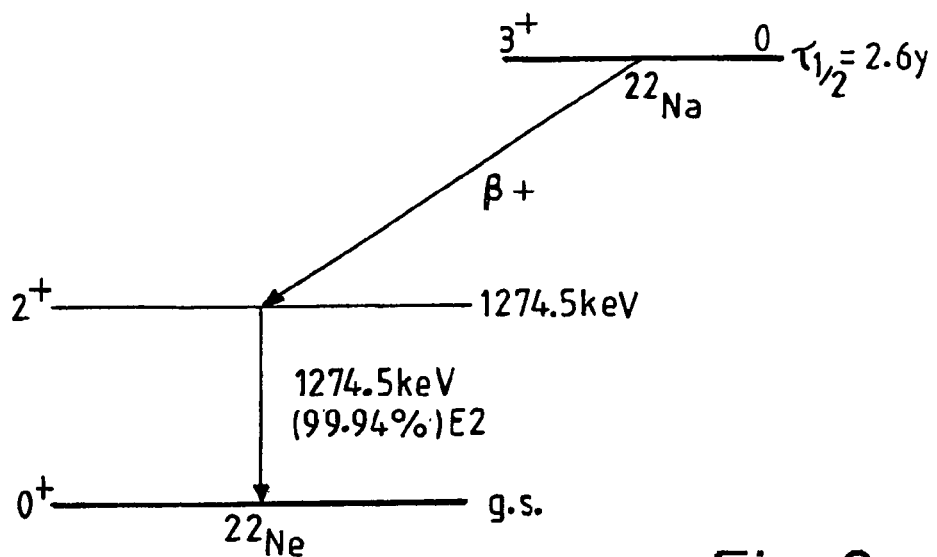
FIG. 3 shows the decay scheme for a preferred photon source used in the tool of FIG. 2.

In the case of positron emitters, the decay particle annihilates with an electron in surrounding matter, with the particle rest masses (511 keV/c$^2$ for each of the annihilating e$^+$e$^-$ pair) converted to energy in the form of electromagnetic radiation. The typical momenta of the emitted positron and the annihilation electron are small compared to the momentum of the released mass energy, and therefore a pair of back-to-back photons, each of energy 511 keV, is created to conserve both momentum and energy. In the case of $^{22}$Na, a gamma ray of energy 1275 keV is also emitted in the de-excitation of the $^{22}$Ne daughter isotope. The decay scheme for $^{22}$Na is shown in FIG. 3.

The tool 50 further includes two similar photon detectors 62, similar to the detector 22 of the tool 10 of FIG. 1. The detectors 62 are disposed at the respective other ends of the measurement portions 54 of the flow-path 52, so that each photon of an annihilation pair must pass longitudinally along a respective measurement portion, through the fluid, before reaching the respective detector. The detectors 62 are diametrically opposed with respect to the photon source 60. Ideally, the distance to each detector is the same, although other arrangements may have advantages in certain circumstances, as will hereinafter be explained.

Figure 2A:
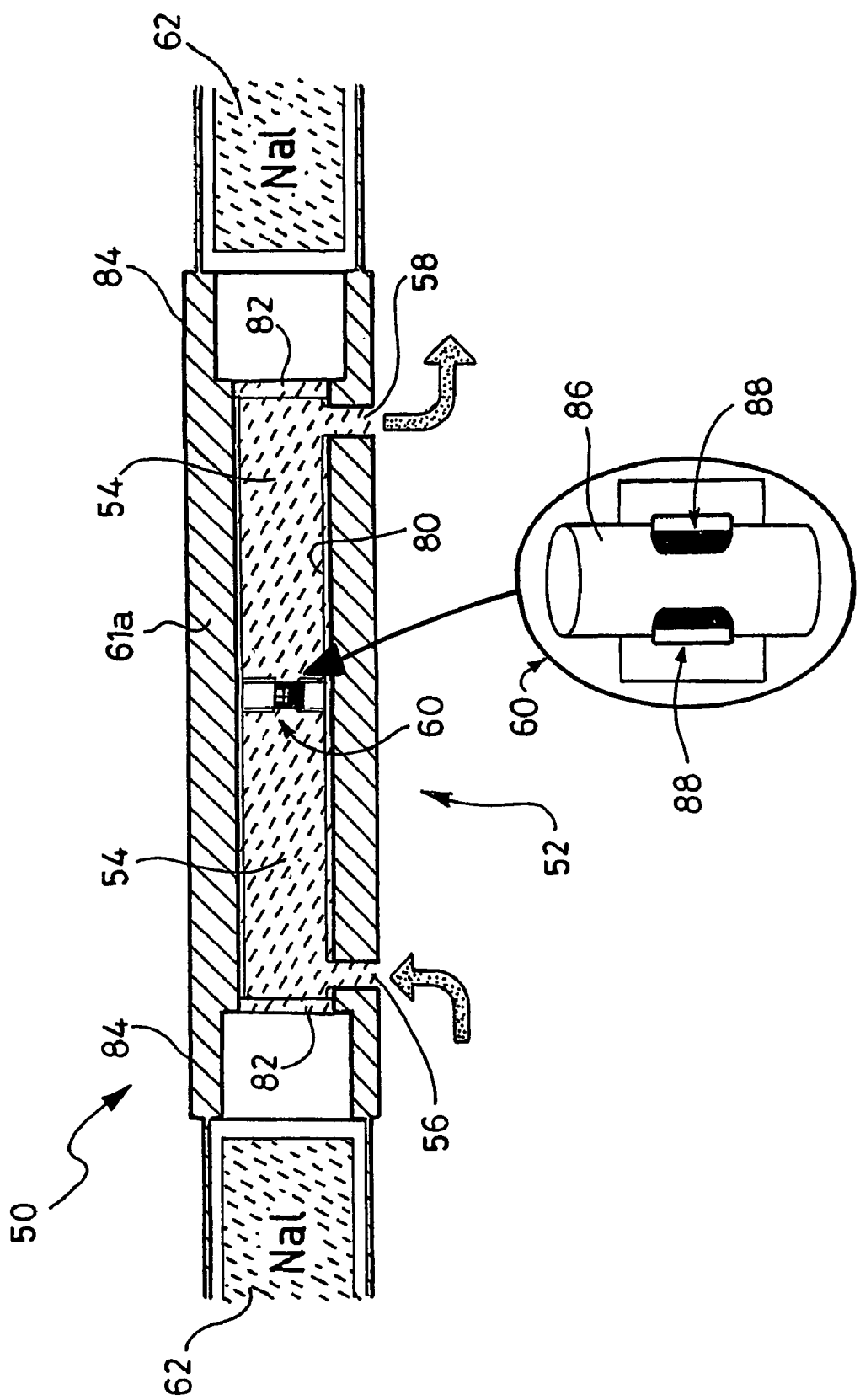
FIG. 2A shows a preferred embodiment of a principal part of the tool of FIG. 1.

FIG. 2A shows a practical implementation of the main flow line 52 and associated components of the tool 50, like components being designated by the same reference numbers as were used in FIG. 2. Thus the flow line 52 and the measurement portions 54 are formed as a single straight tube 80 with titanium end caps 82, with the inlet and outlet portions 56, 58 extending radially of the tube at each end of the tube. The collimators 61 are formed in one piece, indicated at 61a, which has extensions 84 at each end. The extensions 84 extend a little beyond the titanium end caps 82 on the tube 80, and have an increased internal diameter (in relation to the main part of the collimator 61), while the detectors 62 are positioned at the extremities of respective ones of the extensions 84, facing respective ones of the titanium end caps.

The source 60 is double-encapsulated to withstand 25 kPSI, and is mounted in a tubular source holder 86 which is mounted so as to extend diametrically across the tube 80 midway along the length of the tube, with the source 60 positioned substantially on the axis of the tube. The tubular source holder 86 has oppositely disposed cutaway windows 88 facing in opposite directions along the axis of the tube 80, towards the detectors 62

The respective outputs of the detectors 62 of the tool 50 are analysed in terms of energy and timing by signal processing circuitry 64. The circuitry 64 comprises two similar signal processing chains, each comprising an amplifier 65, a single channel analyzer 66 which selects only those outputs from the respective detector corresponding to photons within a certain energy range, and an adjustable delay circuit 68, all connected in series. A respective one of these signal processing chains is connected between a respective detector 62 and a respective input of a coincidence circuit 70, which produces an output only in response to coincident photons in the selected energy range. The output of the coincidence circuit is applied to a counter/scaler and data acquisition/transmission unit 72.

For a $^{22}$Na source of activity S Bq (decays/s), 2S photons per second of energy 511 keV each are produced. The single 511 keV photon count rate in each detector 62 of a symmetrical, identical pair of detectors can then be written as $$n_1 = 2S(\sigma/4\pi)\epsilon_1\epsilon_w exp(-\mu\rho x)$$

where $\sigma$ is the solid angle subtended by each detector, $\epsilon_1$ is the detection efficiency of the detector, $\epsilon_w$ describes the transmission through the wall of the source container and the walls of the flow-line 52, and each photon beam passes through an attenuation path length x. Losses in the wall of the source container and in the flow-line walls can be kept to a very low level. Loss of photon flux in the fluid, represented by the exponential term, is of course desirable, since it provides the measurement signal. As already mentioned, the coincidence circuit 70 produces an output for each coincident photon event detected in both detectors: a coincidence count rate can be derived as follows. The source activity and solid angle do not feature again, since each photon reaching the first detector 62 is accompanied by a partner emitted at 180°, i.e. towards the second detector 62. The coincidence rate is lower than $n_1$ in proportion to the efficiency of the second detector 62 ($\epsilon_2$) and the transmission efficiency through the flow-line walls of the second photon. Crucially, however, the coincidence rate is also reduced by a factor of $e^{-\mu\rho x}$ due to attenuation in fluid in the second measurement portion 54 of the flow-line 52.

Thus the count rate for coincident two-photon events can be written as:

$$n_{coin} = 2S(\sigma/4\pi)\epsilon_1\epsilon_2\epsilon_w\epsilon_w exp(-\mu\rho x)exp(-\mu\rho x)exp(-\mu\rho x)$$

or $$n_{coin} = 2S(\sigma/4\pi)\epsilon_1\epsilon_2\epsilon_w\epsilon_w exp(-\mu\rho 2x)$$

It can thus be seen that the coincidence rate has density contrast equivalent to a path length of 2x, while achieving solid angle efficiency $\sigma$ corresponding to an attenuation length of only x. This gives an increase in count rate efficiency of a factor of 4 compared to a single photon measurement with the same density sensitivity, although small losses will be introduced due to the efficiency of the second detector and losses in transmission of the second photon through the flow-line walls. These losses can be made to be relatively small. With an electronic coincidence requirement, a very wide spectroscopy window can be applied to each detector, requiring only the suppression of low energy noise and the high-energy 1275 keV photon. With thin walls of strong, low-density materials, the transmission through the flow-line walls may be close to 100%.

Importantly, the innovative features of the tool 50 permit an extremely compact geometry to be achieved, with detectors subtending a relatively large solid angle, while maintaining a relatively long effective attenuation path length.

However, many modifications can be made to the tool 50, in order that certain other advantages are also achieved.

Figure 4:
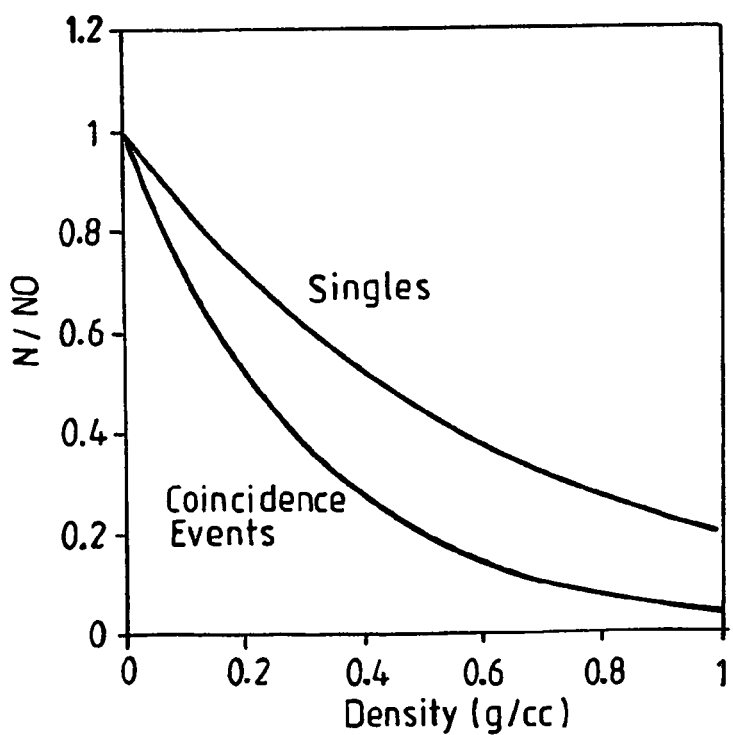
FIG. 4 is a graph of showing the how photon count rates vary with density for single and coincident photon detection in the tool of FIG. 2.
Figure 5:
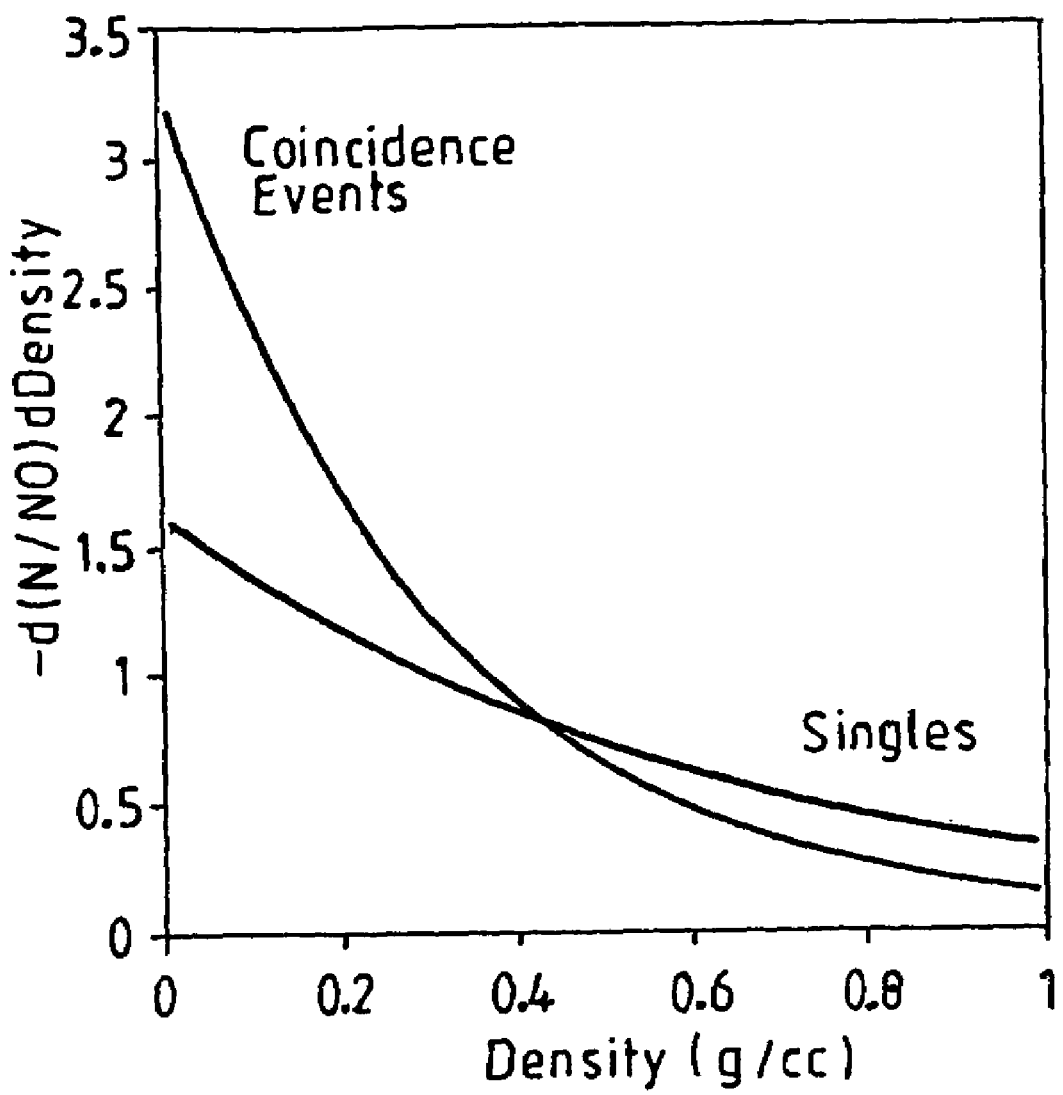
FIG. 5 is a graph of relative density sensitivity for single and coincident photon detection in the tool of FIG. 2.

Thus, FIG. 4 shows the relative count rates for singles events (511 keV photons registering in either detector 62) and coincidence events (a 511 keV photon registering in both detectors 62 within a short time window) normalised to the count rate for an empty sample volume ($n_0$). Because of the exponential nature of the response function, the sensitivity of the coincidence measurement decreases with increasing attenuation. So the precision of measurements for densities in the range 0.5–1.0 g/cc is lower than for densities below 0.5 g/cc. Optimal ranges can be selected by a choice of appropriate path length in each sample volume. The response can be increased at high densities by choosing a shorter attenuation path, which is possible by measuring also singles events (with photons passing through only one arm of the sample fluid), where the requirement is only that at least one detector of the pair registers an event. FIG. 5 shows the measurement sensitivity, ie the negative gradient of the count rate curves of FIG. 4, as a function of density. The graph shows clearly that, for a suitably chosen geometry, a coincidence measurement has twice the sensitivity of a singles measurement at low densities, while at higher densities (~0.8–1.0 g/cc) the reverse is the case. In practice, an intelligent interpretation algorithm is used to choose the more appropriate interpretation mode.

The dynamic range of the measurement can be further extended by using single 1275 keV events to measure very high densities, since these photons exhibit a lower attenuation coefficient. By an appropriate choice of sample volume length, the tool can be optimised for the highest precision from coincident 511 keV events at low densities, singles 511 keV events at intermediate energies, and single 1275 keV events at the highest energies. In this implementation of the invention, at least one of the single channel analysers 66 of FIG. 2 is replaced by a multichannel analyser producing outputs for both 511 keV events and 1275 keV events.

Additionally, it is possible to make a determination of the $^{22}$Na source activity by measuring the count rate in the so-called "sum peak", where a 1275 keV photon deposits its full energy in the detector crystal simultaneously with one of the 511 keV photons, giving an event of sum energy 1786 keV. The count rates for the 511 keV peak, the 1275 keV peak and the sum peak can be written as follows:

$$n_{511} = 2S(\sigma/4\pi)\epsilon_{511}$$

$$n_{1275} = S(\sigma/4\pi)\epsilon_{1275}$$

$$n_{sum} = 2S(\sigma/4\pi)\epsilon_{511}(\sigma/4\pi)\epsilon_{1275}$$

Combining these gives $$\frac{n_{511} \cdot n_{1275}}{n_{sum}} = \frac{2S^2(\sigma/4\pi)^2 \epsilon_{511}\epsilon_{1275}}{2S(\sigma/4\pi)^2 \epsilon_{511}\epsilon_{1275}}$$

$$S = \frac{n_{511} \cdot n_{1275}}{n_{sum}}$$

Thus it is possible to maintain an online source activity calibration, and to implement an alarm to replace the source when its activity has dropped significantly. The half-life of $^{22}$Na is 2.6 years.

Many other modifications can be made to the described embodiments of the invention.

For example, multi-line gamma ray photon sources other than $^{22}$Na or $^{133}$Ba can be used, eg $^{60}$Co. In the case of $^{133}$Ba and $^{60}$Co sources, the photons are not emitted back-to-back, so that it is not strictly necessary for the source and detectors to be aligned in a straight line, as in the tool 50. However, since this arrangement is advantageous for compactness reasons, it is likely to be preferred.

And although the described embodiments of the invention use licence-exempt gamma ray sources, the use of an X-ray source, in the form of a downhole X-ray generator, is also possible. While such a source is more complex and expensive, and has certain other disadvantages in relation to the preferred gamma ray source, it also has certain advantages, particularly with regard to sensitivity to fluid density and the statistical precision of the measurement.

The invention claimed is:

1. Apparatus for measuring the density of a fluid, the apparatus comprising:
   means defining a flow path for the fluid;
   a gamma photon source;
   photon detector means positioned to receive photons from the gamma photon source via the fluid in said flow path; and
   means for determining the density of the fluid from a count rate of the photons received by the detector means;
   wherein the gamma photon source comprises a source which emits coincident photon pairs, the flow path comprises two relatively straight measurement portions extending in the direction of flow of the fluid and substantially aligned with each other each disposed to receive a respective photon of each pair, the gamma photon source is disposed between the adjacent ends of the two relatively straight measurement portions, the detector means comprises two detectors each arranged to receive photons which have passed along a respective measurement portion, and the density determining means determines the density of the fluid from the count rate of coincident photon pairs detected by the detectors.

2. Apparatus as claimed in claim 1, wherein the two measurement portions are substantially equal in length.

3. Apparatus as claimed in claim 1, wherein the gamma photon source comprises a positron emitter.

4. Apparatus as claimed in claim 3, wherein the gamma photon source is $^{22}$Na.

5. Apparatus as claimed in claim 4, further comprising means responsive to the photon detector means for counting the detected additional photons emitted on the de-excitation of the $^{22}$Ne daughter isotope resulting from the decay of the $^{22}$Na source.

6. Apparatus as claimed in claim 5, wherein the density determining means is further arranged to determine the density of the fluid from the count rate of said detected additional photons.

7. Apparatus as claimed in claim 4, further comprising means responsive to the photon detector means measuring the count rate in the sum peak of the source, whereby to determine the activity of the source.

8. A method of measuring the density of a fluid, the method comprising the steps of:
   defining a flow path for the fluid;
   irradiating the fluid in the flow path with photons from a gamma photon source;
   detecting photons which have passed through the fluid in the flow path; and
   determining the density of the fluid from a count rate of the detected photons;
   wherein the irradiating step comprises providing a gamma photon source which emits coincident photon pairs, the flow path defining step comprises providing said flow path with first and second relatively straight measurement portions with each of the relatively straight measurement portions extending in the direction of flow of the fluid and substantially aligned with each other and each of the relatively straight measurement portions being disposed to receive a respective photon of each pair for transmission therealong, and the density determining step comprises determining the density of the fluid from the count rate of coincident photon pairs detected.

9. A method as claimed in claim 8, wherein the density determining step comprises, for an upper part of the expected range of densities to be measured, determining the density of the fluid from the count rate of the photons passing along only one of said measurement portions.

10. A method as claimed in claim 8, wherein the gamma photon source is $^{22}$Na, and further comprising the step of counting the detected additional photons emitted on the de-excitation of the $^{22}$Ne daughter isotope resulting from the decay of the $^{22}$Na source.

11. A method as claimed in claim 10, further comprising determining the density of the fluid from the count rate of the detected additional photons.

12. A method as claimed in claim 8, further comprising measuring the count rate in the sum peak of the source, whereby to determine the activity of the source.

* * * * *